United States Patent [19]

Bartmann et al.

[11] Patent Number: 4,601,851

[45] Date of Patent: Jul. 22, 1986

[54] CYCLODODEC-2-ENYL ETHERS IN FRAGRANCE COMPOSITIONS

[75] Inventors: Martin Bartmann, Recklinghausen; Klaus Burzin, Marl, both of Fed. Rep. of Germany

[73] Assignee: Huels Aktiengesellschaft, Marl, Fed. Rep. of Germany

[21] Appl. No.: 569,005

[22] Filed: Jan. 9, 1984

[30] Foreign Application Priority Data

Jan. 7, 1983 [DE] Fed. Rep. of Germany ....... 3300341

[51] Int. Cl.$^4$ ...................... A61K 7/46; C07F 43/184
[52] U.S. Cl. .................................. 252/522 R; 568/667
[58] Field of Search ..................... 252/522 R

[56] References Cited

U.S. PATENT DOCUMENTS

| | | | |
|---|---|---|---|
| 3,235,601 | 2/1966 | Parsons et al. | 252/522 R X |
| 3,240,812 | 3/1966 | Lafont et al. | 252/522 R X |
| 3,318,945 | 5/1967 | Erman | 252/522 R X |
| 3,754,036 | 8/1973 | Blumenthal | 252/522 R X |
| 3,754,039 | 8/1973 | Nageli | 252/522 R X |
| 3,816,349 | 6/1974 | Hall | 252/522 R |
| 3,876,561 | 4/1975 | Naegeli | 252/522 R |
| 4,460,498 | 7/1984 | Giersch et al. | 252/522 R |

OTHER PUBLICATIONS

Randerbrock, Rudolf "Das Polaritatsprofil als Mittel zur Geruchsbeurteilung", Vorgetragen am 8, Mai, 1965, J. Soc. Cosmetic Chemists, pp. 652–671.

Kastner, D., "The Verbal and Non-Verbal Description of Scents", From—Perfume Oils for Cosmetics and Industry, Munich-Solln.

Grandi et al., "Base-Induced Decomposition of Cyclic Conjugated p-Tosylhydrazones: A Novel Route to [n>9] (3,5) Pyrazolophanes", J. Chem. Research(S), 1979, pp. 246–247.

Primary Examiner—Anton H. Sutto
Attorney, Agent, or Firm—Millen & White

[57] ABSTRACT

Cyclododec-2-enyl ethers having the formula

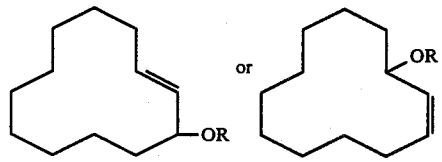

wherein R is a straight or branched chain $C_{1-4}$ alkyl or alkenyl group, have fragrance characteristics similar to patchouli oil, and are attractive compounds for use in the manufacture of fragrance compositions.

12 Claims, No Drawings

CYCLODODEC-2-ENYL ETHERS IN FRAGRANCE COMPOSITIONS

BACKGROUND OF THE INVENTION

One of the most important components of known fragrance compositions is patchouli oil, obtained from the leaves of Pogostemon cablin Benth. occurring in Malaysia. Almost all of the conventional perfume sprays, deodorant sprays, and perfumes contain this fragrance component, which is capable of decisively impressing its character on the note of a fragrance, in proportions of between 0.1 and 50% by weight.

Efforts have been made for quite some time to replace the concentrate, consisting of at least 24 ingredients, by a more readily producible material. The attempts made heretofore must be considered unsatisfactory. Although it has been asserted that 3-methyl-9-methyleneendo-tricyclo[5.2.1.0$^{2,6}$]dec-3-en-8(exo)-ol "is said to reproduce several of the typical fragrance notes" (cf. DOS No. 3,120,700), this complex compound is unsuited as a substitute for patchouli oil, if for no other reason than that its manufacture is much too expensive.

The methyl ether of cyclododec-2-en-1-ol is known. This compound was characterized structurally and spectrometrically during the course of a study of the alkaline decomposition of cyclic, conjugated p-tosylhydrazones (Grandi et al., J. Chem. Res. (S), 1979, 246). There is no mention in this reference regarding possible fragrance properties.

OBJECTS OF THE INVENTION

One object of this invention is to provide readily accessible compounds capable of entirely or partially replacing natural patchouli oil in fragrance compositions.

Another object of the invention is to provide fragrance compositions containing the ethers of the invention.

Upon further study of the specification and appended claims, further objects and advantages of this invention will become apparent to those skilled in the art.

SUMMARY OF THE INVENTION

It has now been found that ethers of cyclododec-2-en-1-ol with alcohols of the formula ROH, wherein R is a straight or branched chain $C_{1-4}$ alkyl or $C_{2-4}$ alkenyl group, satisfy these requirements. All but the methyl ether are novel and none were heretofore known as fragrance components.

DETAILED DISCUSSION

The ethers of this invention, with their intensive, long-lasting, spicy and slightly aldehydric note, are attractive substitutes for natural patchouli oil. Their fragrance note is surprising inasmuch as the structurally related ethers of cyclododecanol (U.S. Pat. Nos. 3,281,474; 3,845,141; and Dos No. 2,928,098) and of cyclododecylmethanol (U.S. Pat. No. 4,359,588) are characterized by a woody and/or woody-ambergris fragrance, respectively, and are not sufficiently similar in fragrance characteristics to natural patchouli oil to serve as a replacement therefor.

The synthesis of the ethers of the invention can be effected starting with the unsaturated, twelve-membered ring alcohol, cyclododec-2-en-1-ol, which, in turn, can be obtained from cis- or trans-cyclododecene by conventional allylic oxidation with selenium dioxide, e.g., by using an analogous procedure to that disclosed in J. Am. Chem. Soc. 93, 4835 (1971).

Another process for the preparation of the allylic alcohol comprises passing the epoxide of cis- or trans-cyclododecene over lithium phosphate, using an analogous procedure to that disclosed in U.S. Pat. No. 2,426,264.

In one method of preparing ethers according to the invention, cyclododec-2-en-1-ol is converted to its alcoholate conjugate base by a strong base, such as, for example, a metal hydride, a metal amide, or potassium tert-butylate. It is recommended to utilize an inert organic solvent, such as, for example, aliphatic or aromatic hydrocarbons. Reaction with about a 20% excess of sodium amide in boiling xylene is particularly advantageous. After adding a suitable electrophile, preferably about a 20% excess thereof, and heating for about four hours at 140° C., the reaction is quenched by treatment with cold NaOH solution. Suitable electrophiles include, e.g., sulfonic acid esters, alkyl halides, especially the bromides and iodides, and especially dialkyl sulfates. Dimethyl sulfate is preferred for preparing the methyl ether. The reaction product is isolated by a conventional workup, e.g., by washing the organic phase with water, drying, and fractional distillation.

According to a second method, a mixture of the alcohols on which the ether is based is heated in the presence of catalytic amounts of concentrated sulfuric acid, e.g., about 1–30 mole %. It is advantageous in many cases to add copper(I) chloride in order to accelerate the reaction preferably about 2–25 g per mole of cyclododecenol. The alcohol of the formula ROH is preferably employed in excess. Again, isolation of the product is effected by conventional workup. The yield is above 70%.

The cyclododec-2-en-1-yl ethers are obtained, according to both methods, in a purity of more than 98% as a racemic mixture of cis/trans-isomers. The cis/trans-isomer proportion is not critical. One or more of these ethers can be utilized in this form to impart a patchouli-like spicy, slightly aldehydic fragrance note to any composition in which they are incorporated, e.g., in an amount of 0.1–50% by weight. Insofar as desired, the geometric isomers can be separated and/or further purified by careful fractional distillation. Enantiomers can be separated and isolated by conventional techniques, if desired, e.g., at the cyclododecenol stage, prior to the Williamson ether synthesis. Pure enantiomers, racemic mixtures of pure cis- or trans-isomers, or mixtures of enantiomers and/or cis- or trans-isomers of the ethers of the invention are all embraced within the scope of the invention, both with respect to the compounds per se and with respect to fragrance compositions containing them.

The ethers of this invention are readily compatible with other fragrance compounds or ingredients of composito to which they may be added, except for compounds which are so strongly acidic as to decompose the allylic ethers of the invention. Their proportion in fragrance compositions can range between 0.5 and 50% by weight. On account of their fragrance properties, the methyl and ethyl ethers of cyclododec-2-en-1-ol are preferred.

As used herein, the term "fragrance composition" means a blend consisting essentially of a plurality of fragrance compounds and/or essential oils, each of which has distinctive fragrance characteristics, the blend having a fragrance that partakes of the characteristics of its constituent fragrance components. A fragrance composition may also contain non-fragrance ingredients or ingredients which merely enhance the fragrance characteristics of the fragrance components, e.g., carriers, solvents, perfume, powder, cream or lotion bases, stabilizers, preservatives, normally gaseous aerosol propellants, and the like. Conversely, a "fragrance composition" is not meant to include the reaction mixture from tosylhydrazone decomposition, containing the methyl ether of cyclododec-2-en-1-ol (Grandi et al., supra).

Illustrative of the many fragrance compounds, essential oils and art-recognized additives in combination with which the ethers of the invention may be formulated in fragrance compositions are those disclosed in the following representative publications, all of which, together with references noted therein, are incorporated herein by reference: St. Arctander, "Perfume and Flavor Chemicals" (edited by the author Montclair, N.J., 1969); Snell et al., "Dictionary of Commercial Chemicals, 3d. Ed.", Chapter 33(Van Nostrand, Princeton, N.J., 1962); H. Aebi, E. Baumgartner, H. P. Fiedler, and G. Ohloff, "Kosmetika, Riechstoffe und Lebensmittelzusatzstoffe", Georg Thieme Verlag, Stuttgart, 1978.

It is to be understood, moreover, that such publications are not inclusive, inasmuch as the present invention will also be useful for the formulation of fragrance compositons with fragrance compounds or essential oils which may be discovered in the future or which are not described in these references.

The fragrance compositions or one or more of the ethers of the invention can serve directly as a perfume or for the perfuming of any composition to which it is desired to impart a fragrance, e.g., cosmetics or toiletries, e.g., creams, soaps, lotions, deodorants, hair sprays, shaving creams, shampoos, talcum powders and the like; or to improve the aroma of industrial products, e.g., detergents, polishing and cleaning agents, room deodorants, disinfectants, auxiliary agents for textiles and the like.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Examples 1-4 describe the production of representative aliphatic ethers of this invention wherein R is methyl, ethyl, allyl, and isopropyl. Examples 5 and 6 disclose illustrative fragrance compositions.

EXAMPLE 1

Cyclododec-2-enyl Methyl Ether 25 g (0.65 mol) of sodium amide was introduced into 150 ml of xylene and heated to boiling under agitation. Over one hour, 92 g (0.5 mol) of cyclododec-2-enol, dissolved in 750 ml of xylene, was added dropwise to the boiling suspension. In order to complete the alcoholate formation, the mixture was heated under reflux for another two hours. Subsequently, 44 g (0.35 mol) of dimethyl sulfate was added dropwise thereto. The reaction mixture was held under reflux for another four hours and then poured into a mixture of ice and 35 g of sodium hydroxide. The organic phase was washed with water, dried with $Na_2SO_4$, and then distilled.

Boiling point (0.8 mbar): 99° C.
Yield: 87%
IR: 1635, 1100, 970 cm$^{-1}$
NMR (CCl$_4$): 5.75-5.2 $\delta$ (2H); 3.25 $\delta$ (S, 3H); 3.5 $\delta$ (1H)

The cyclododec-2-enyl methyl ether exhibits a spicy, slightly aldehydic fragrance.

EXAMPLE 2

Cyclododec-2-enyl Ethyl Ether

In an agitated flask, 64 g (0.25 mol) of cyclododec-2-en-1-ol, 250 g of ethanol, and 2.5 g of $Cu_2Cl_2$ were mixed together. Then 2.5 g of $H_2SO_4$ (concentrated) was gently added dropwise thereto, and the reaction mixture was heated to boiling for one hour. The excess ethanol was thereafter removed by distillation, the residue was taken up in 300 ml of n-hexane, and this solution was washed with 10% strength soda solution and then water so that it became neutral. After drying over $Na_2SO_4$, the hexane was removed by means of a rotary evaporator, and the product was isolated by fractional vacuum distillation.

Boiling point (0.3 mbar): 90° C.
Yield: 90%
IR: 1635, 1100, 970 cm$^{-1}$
NMR (CCl$_4$): 5.75-5.2 $\delta$ (2H); 3.7-3.3 $\delta$ (m, 3H); 1.2 $\delta$ (t, 3H)

The cyclododec-2-enyl ethyl ether has an intensive spicy, slightly aldehydic fragrance and is reminiscent of natural patchouli oil.

EXAMPLE 3

Cyclododec-2-enyl Allyl Ether

The cyclododec-2-enyl allyl ether was obtained in accordance with the procedure of Example 2 by reacting 64 g (0.25 mol) of cyclododec-2-en-1-ol with 313 g (5.4 mol) of allyl alcohol.

Boiling point (0.1 mbar): 110° C.
Yield: 72%
IR: 1635, 1100, 990, 970, 920 cm$^{-1}$
NMR (CCl$_4$): 6.0-5.0 $\delta$ (m, 5H); 4.05-3.6 $\delta$ (m, 3H)

EXAMPLE 4

Cyclododec-2-enyl Isopropyl Ether

The cyclododec-2-enyl isopropyl ether was obtained in accordance with the procedure of Example 2 by reaction of 64 g (0.25 mol) of cyclododec-2-en-1-ol with 324 g (5.4 mol) of isopropyl alcohol.

Boiling point (0.1 mbar): 106° C.
Yield: 75%
IR: 1635, 1100, 970 cm$^{-1}$
NMR (CCl$_4$): 5.75-5.2 $\delta$ (2H); 3.9-3.6 $\delta$ (m, 2H); 1.2 $\delta$ (d, 6H)

EXAMPLE 5

| Floral Phantasy Composition | Wt. Pts. |
| --- | --- |
| Cyclododec-2-enyl ethyl ether | 100 |
| 7-Hydroxy-6,7-dihydrocitronellol | 150 |
| 2-Phenylethanol | 50 |
| 3-Phenylpropanol | 50 |
| Ylang-ylang (synthetic) | 50 |
| 2,5-Dioxacyclohexadeca-1,6-dione | 50 |
| Linalool | 200 |
| Linalyl acetate | 150 |

| Floral Phantasy Composition | Wt. Pts. |
| --- | --- |
| Benzyl acetate | 50 |
| Bergamot (synthetic) | 50 |
| Mixture of 1-(3,4-epoxy-4-methyl-pentyl)-4- and -5-formylcyclohexane | 100 |
| | 1,000 |

EXAMPLE 6

| Oriental Fragrance Composition | Wt. Pts. |
| --- | --- |
| Cyclododec-2-enyl methyl ether | 100 |
| Coumarin | 30 |
| Bergamot oil | 50 |
| Geraniol | 100 |
| Citronellol | 100 |
| 2-Phenylethanol | 120 |
| Geranium oil, Bourbon | 30 |
| Benzoin | 20 |
| Styrax | 20 |
| Oakmoss extract | 10 |
| 2-Pentylcinnamic aldehyde | 80 |
| Benzyl acetate | 100 |
| α-Methylionone | 65 |
| Sandalwood oil (East Indian) | 20 |
| 4-tert-Butylcyclohexyl acetate | 50 |
| Lavandin oil | 50 |
| 2,5-Dioxacyclohexadeca-1,6-dione | 55 |
| | 1,000 |

Compounds such as ylang-ylang, etc., where the names do not directly reveal the structure, are described in the book by St. Arctander "Perfume and Flavor Chemicals" Montclair N.J., U.S.A., 1969.

Each of the ethers of the invention has a somewhat different fragrance profile from the others, and imparts slightly different notes to compositions to which it is added. Thus, cyclododec-2-enyl $C_{1-4}$ alkyl and/or alkenyl ethers wherein R is a methyl, ethyl, propyl, isopropyl, n-butyl, isobutyl, sec-butyl, tert-butyl, vinyl, propenyl or butenyl group will each have significant fragrance characteristics that differ from other ethers of the generic class of the invention. One or more of these ethers may be added to fragrance compositions depending upon the desired fragrance and use.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a fragrance composition consisting essentially of a plurality of fragrance components, the improvement wherein at least one such fragrance component is a straight or branched chain $C_{1-4}$ alkyl or $C_{2-4}$ alkenyl ether of cyclododec-2-en-1-ol, in an amount sufficient to impart to said composition an intensive, long-lasting, spicy and slightly aldehydic note similar to that imparted by natural patchouli oil.

2. A fragrance composition according to claim 1, wherein said ether is methyl cyclododec-2-enyl ether.

3. A fragrance composition according to claim 1, wherein said ether is ethyl cyclododec-2-enyl ether.

4. A fragrance composition according to claim 1, wherein said amount is 0.5–50% by weight.

5. A fragrance composition according to claim 2, wherein said amount is 0.5–50% by weight.

6. A fragrance composition according to claim 3, wherein said amount is 0.5–50% by weight.

7. A method of imparting to a composition a spicy, slightly aldehydic note similar to that of natural patchouli oil, comprising incorporating in said composition an effective fragrance-imparting amount of at least one straight or branched chain $C_{1-4}$ alkyl or alkenyl ether of cyclododec-2-en-1-ol.

8. A method according to claim 7, wherein said ether is methyl cyclododec-2-enyl ether.

9. A method according to claim 7, wherein said ether is ethyl cyclododec-2-enyl ether.

10. A method according to claim 7, wherein said amount is 0.1–50% by weight.

11. A method according to claim 8, wherein said amount is 0.1–50% by weight.

12. A method according to claim 9, wherein said amount is 0.1–50% by weight.

* * * * *